US006815538B2

(12) United States Patent
Walke et al.

(10) Patent No.: US 6,815,538 B2
(45) Date of Patent: Nov. 9, 2004

(54) HUMAN SECRETED PROTEINS AND POLYNUCLEOTIDES ENCODING THE SAME

(75) Inventors: D. Wade Walke, Spring, TX (US); Nathaniel L. Wilganowski, Houston, TX (US); C. Alexander Turner, Jr., The Woodlands, TX (US); Erin Hilbun, Spring, TX (US); Xiaoming Wang, Palatine, IL (US); Gregory Donoho, The Woodlands, TX (US); John Scoville, Houston, TX (US)

(73) Assignee: Lexicon Genetics Incorporated, The Woodlands, TX (US)

( * ) Notice: Subject to any disclaimer, the term of this patent is extended or adjusted under 35 U.S.C. 154(b) by 112 days.

(21) Appl. No.: 09/813,290

(22) Filed: Mar. 20, 2001

(65) Prior Publication Data

US 2002/0042504 A1 Apr. 11, 2002

Related U.S. Application Data

(60) Provisional application No. 60/193,639, filed on Mar. 31, 2000, provisional application No. 60/191,188, filed on Mar. 22, 2000, and provisional application No. 60/190,638, filed on Mar. 20, 2000.

(51) Int. Cl.$^7$ .............................................. C07H 21/04
(52) U.S. Cl. .................. 536/23.2; 536/23.2; 536/23.1; 530/300; 435/325; 435/252.3; 435/320.1; 435/69.1
(58) Field of Search ............................... 536/23.2, 23.1, 536/23.5, 350; 530/350, 300; 514/2, 12; 435/69.1, 320.1, 252.3, 325

(56) References Cited

U.S. PATENT DOCUMENTS

| | | |
|---|---|---|
| 4,215,051 A | 7/1980 | Schroeder et al. |
| 4,376,110 A | 3/1983 | David et al. |
| 4,594,595 A | 6/1986 | Struckman |
| 4,631,211 A | 12/1986 | Houghten |
| 4,689,405 A | 8/1987 | Frank et al. |
| 4,713,326 A | 12/1987 | Dattagupta et al. |
| 4,946,778 A | 8/1990 | Ladner et al. |
| 5,252,743 A | 10/1993 | Barrett et al. |
| 5,424,186 A | 6/1995 | Fodor et al. |
| 5,445,934 A | 8/1995 | Fodor et al. |
| 5,459,127 A | 10/1995 | Felgner et al. |
| 5,556,752 A | 9/1996 | Lockhart et al. |
| 5,700,637 A | 12/1997 | Southern |
| 5,744,305 A | 4/1998 | Fodor et al. |
| 5,837,458 A | 11/1998 | Minshull et al. |
| 5,869,336 A | 2/1999 | Meyer et al. |
| 5,877,397 A | 3/1999 | Lonberg et al. |
| 5,935,865 A | 8/1999 | Goodman et al. |
| 5,948,767 A | 9/1999 | Scheule et al. |
| 5,981,222 A | 11/1999 | Jacobs et al. |
| 6,075,181 A | 6/2000 | Kucherlapati et al. |
| 6,110,490 A | 8/2000 | Thierry |
| 6,150,584 A | 11/2000 | Kucherlapati et al. |

FOREIGN PATENT DOCUMENTS

| | | |
|---|---|---|
| EP | 0896058 A1 | 2/1999 |
| EP | 0960888 A1 | 12/1999 |
| EP | 0960937 A1 | 12/1999 |
| WO | WO 98/25504 A1 | 5/1998 |
| WO | WO 99/45114 A2 A3 | 9/1999 |
| WO | WO 00/49134 A1 | 8/2000 |

OTHER PUBLICATIONS

Database EMBL 'Online' EMBO Heidelberg, DE; Oct. 1, 2000, Seki M. et al., "Semaphorin–sem2 (human)" retrieved from EMBL Database accession No. q9ns98, XP002177219, abstract.

Database EMBL 'Online' EMBO Heidelberg, DE; Mar. 1, 2001, O'Hara O. et al., "FLJ0014 Protein (Fragment)" retrieved from EMBL Database accession No. q9h7q3, XP002177220, abstract.

Shirozu et al., "Characterization of Novel Secreted and Membrane Proteins Isolated by the Signal Sequence Trap Method," Genomics, Academic Press, San Diego, vol. 37, No. 3, Nov. 1, 1996, pp. 273–280, XP002054773.

Jacobs, K. et al., "A novel Method for Isolating Eukaryotic CDNA Clones Encoding Secreted Proteins," Journal of Cellular Biochemistry—Supplement, Wiley–Liss, US, vol. 21A, Mar. 10, 1995, p. 19, XP002027246, ISSN: 0730–2312.

International Search Report, International Application No. PCT/US01/08834, Oct. 8, 2001 (Attorney Docket No. LEX–0151–PCT).

Bird et al, 1988, "Single–Chain Antigen–Binding Proteins", Science 242:423–426.

Bitter et al, 1987, "Expression and Secretion Vectors for Yeast", Methods in Enzymology 153:516–544.

Colbere–Garapin et al, 1981, "A New Dominant Hybrid Selective Marker for Higher Eukaryotic Cells", J. Mol. Biol. 150:1–14.

Gautier et al, 1987, "α–DNA IV:α–anomeric and β–anomeric tetrathymidylates covalently linked to intercalating oxazolopyridocarbazole. Synthesis, physiochemical properties and poly (rA) binding", Nucleic Acids Research 15(16):6625–6641.

Greenspan et al, 1993, "Idiotypes: structure and immunogenicity", FASEB Journal 7:437–444.

Huse et al, 1989, "Generation of a Large Combinatorial Library of the Immunoglobulin Repertoire in Phage Lambda", Science 246: 1275–1281.

(List continued on next page.)

*Primary Examiner*—Christopher R. Tate
*Assistant Examiner*—B. Dell Chism

(57) ABSTRACT

Novel human polynucleotide and polypeptide sequences are disclosed that can be used in therapeutic, diagnostic, and pharmacogenomic applications.

6 Claims, No Drawings

OTHER PUBLICATIONS

Huston et al, 1988, "Protein engineering of antibody binding sites: Recovery of specific activity in an anti–digoxin single–chain Fv analogue produced in *Escherichia coli*", Proc. Natl. Acad. Sci. USA 85:5879–5883.

Inoue et al, 1987, "Sequence–dependent hydrolysis of RNA using modified oligonucleotide splints and R Nase H", FEBS Letters 215(2):327–330.

Inoue et al, 1987, "Synthesis and hybridization studies on two complementary nona(2'–O–methyl)ribonucleotides", Nucleic Acids Research 15(15): 6131–6149.

Inouye & Inyouye, 1985, "Up–promoter mutations in the lpp gene of *Escherichia coli*", Nucleic Acids Research 13(9):3101–3110.

Janknecht et al, 1991, "Rapid and efficient purification of native histidine–tagged protein expressed by recombinant vaccinia virus", PNAS 88:8972–8976.

Kohler & Milstein, 1975, "Continuous cultures of fused cells secreting antibody of predefined specificity", Nature 256:495–497.

Logan et al, 1984, "Adenovirus tripartite leader sequence enhances translation of mRNAs late after infection", Proc. Natl. Acad. Sci. USA 81:3655–3659.

Lowy et al, 1980, "Isolation of Transforming DNA: Cloning the Hamster aprt Gene", Cell 22:817–823.

Morrison et al, 1984, "Chimeric human antibody molecules: Mouse antigen–binding domains with human constant region domains", Proc. Natl. Acad. Sci. USA 81:6851–6855.

Mulligan and Berg, 1981, "Selection for animal cells that express the *Escherichia coli* gene coding for xanthine–guanine phosphoribosyltransferase", Proc. Natl. Acad. Sci. USA 78(4):2072–2076.

Neuberger et al, 1984, "Recombinant antibodies possessing novel effector functions", Nature 312:604–608.

Nisonoff, 1991, "Idiotypes: Concepts and Applications", J. of Immunology 147:2429–2438.

O'Hare et al, 1981, "Transformation of mouse fibroblasts to methotrexate resistance by a recombinant plasmid expressing a prokaryotic dihydrofolate reductase", Proc. Natl. Acad. Sci. USA 78(3): 1527–1531.

Ruther et al, 1983, "Easy identification of cDNA clones", EMBO Journal 2(10):1791–1794.

Santerre et al, 1984, "Expression of prokaryotic genes for hygromycin B and G418 resistance as dominant–selection markers in mouse L cells", Gene 30:147–156.

Sarin et al, 1988, "Inhibition of acquired immunodeficiency syndrome virus by oligodeoxynucleoside methylphosphonates", Proc. Natl. Acad. Sci. USA 85:7448–7451.

Smith et al, 1983, "Molecular Engineering of the *Autographa californica* Nuclear Polyhedrosis Virus Genome: Deletion Mutations within the Polyhedrin Gene", J. Virol. 46(2):584–593.

Stein et al., 1988, "Physiochemical properties of phosphorothioate oligodeoxynucleotides," Nucleic Acids Research 16(8):3209–3221.

Szybalska & Szybalski, 1962, "Genetics of Human Cell Lines, IV. DNA–Mediated Heritable Transformation of a Biochemical Trait", Proc. Natl. Acad. Sci. USA 48:2026–2034.

Takeda et al, 1985, "Construction of chimaeric processed immunoglobulin genes containing mouse variable and human constant region sequences", Nature 314:452–454.

Van Heeke et al, 1989, "Expression of Human Asparagine Synthetase in *Escherichia coli*", J. Biol. Chemistry 264(10):5503–5509.

Ward et al, 1989, "Binding activities of a repertoire of single immunoglobulin variable domains secreted from *Escherichia coli*", Nature 341:544–546.

Wigler et al, 1977, "Transfer of Purified Herpes Virus Thymidine Kinase Gene to Cultured Mouse Cells", Cell 11:223–232.

Wigler et al, 1980, "Transformation of mammalian cells with an amplifiable dominant–acting gene", Proc. Natl. Acad. Sci. USA 77(6):3567–3570.

HUMAN SECRETED PROTEINS AND POLYNUCLEOTIDES ENCODING THE SAME

The present application claims the benefit of U.S. Provisional Application Nos. 60/190,638, 60/191,188 and 60/193,639 which were filed on Mar. 20, 2000, Mar. 22, 2000 and Mar. 31, 2000, respectively. These U.S. Provisional Applications are herein incorporated by reference in their entirety.

INTRODUCTION

The present invention relates to the discovery, identification, and characterization of novel human polynucleotides encoding proteins that share sequence similarity with animal secreted proteins such as, inter alia, semiphorins, protein/peptide hormones of the neurohypophysial and oxytocin (neurophysin 1 precursor) family. The invention encompasses the described polynucleotides, host cell expression systems, the encoded proteins, fusion proteins, polypeptides and peptides, antibodies to the encoded proteins and peptides, and genetically engineered animals that either lack or over express the disclosed polynucleotides, antagonists and agonists of the proteins, and other compounds that modulate the expression or activity of the proteins encoded by the disclosed polynucleotides that can be used for diagnosis, drug screening, clinical trial monitoring, and treatment of diseases and disorders.

BACKGROUND OF THE INVENTION

Secreted proteins are biologically active molecules that have been implicated in a number of biological processes and anomalies such as hyperproliferative disorders, muscle contraction, vasoconstriction and dilation, immunity, development, modulating metabolism, and cancer. In particular, protein hormones have been implicated in, inter alia, autoimmunity, diabetes, osteoporosis, infectious disease, arthritis, and modulating physiological homeostasis, metabolism, and behavior. Examples of biologically active secreted proteins include, but are not limited to, semaphorins which have been implicated in, inter alia, mediating neural processes, cancer, and development. Along with their cognate receptors (i.e., neuropilins), semaphorins act to regulate the organization and fasciculation of nerves in the body.

SUMMARY OF THE INVENTION

The present invention relates to the discovery, identification, and characterization of nucleotides that encode novel human proteins, and the corresponding amino acid sequences of these proteins. The novel human proteins (NHPs) described for the first time herein share structural similarity with semaphorin proteins (SEQ ID NOS: 1–5), protein/peptide hormones of the neurohypophysial family (SEQ ID NOS:6–7) and protein/peptide hormones of the oxytocin (neurophysin 1 precursor) family (SEQ ID NOS:8–10).

The novel human nucleic acid sequences described herein, encode alternative proteins/open reading frames (ORFs) of 875, 782, 91 and 89 amino acids in length (see respectively SEQ ID NOS: 2, 4, 7, 9).

The invention also encompasses agonists and antagonists of the described NHPS, including small molecules, large molecules, mutant NHPS, or portions thereof, that compete with native NHP, peptides, and antibodies, as well as nucleotide sequences that can be used to inhibit the expression of the described NHPs (e.g., antisense and ribozyme molecules, and gene or regulatory sequence replacement constructs) or to enhance the expression of the described NHP polynucleotides (e.g., expression constructs that place the described polynucleotide under the control of a strong promoter system), and transgenic animals that express a NHP transgene, or "knock-outs" (which can be conditional) that do not express a functional NHP. Knock-out mice can be produced in several ways, one of which involves the use of mouse embryonic stem cells ("ES cells") lines that contain gene trap mutations in a murine homolog of at least one of the described NHPS. When the unique NHP sequences described in SEQ ID NOS:1–10 are "knocked-out" they provide a method of identifying phenotypic expression of the particular gene as well as a method of assigning function to previously unknown genes. Additionally, the unique NHP sequences described in SEQ ID NOS:1–10 are useful for the identification of coding sequence and the mapping a unique gene to a particular chromosome.

Further, the present invention also relates to processes for identifying compounds that modulate, i.e., act as agonists or antagonists, of NHP expression and/or NHP activity that utilize purified preparations of the described NHPs and/or NHP product, or cells expressing the same. Such compounds can be used as therapeutic agents for the treatment of any of a wide variety of symptoms associated with biological disorders or imbalances.

DESCRIPTION OF THE SEQUENCE LISTING AND FIGURES

The Sequence Listing provides the sequences of the described NHP ORFs that encode the described NHP amino acid sequences. SEQ ID NOS: 5 and 10 describe NHP ORFs and flanking regions.

DETAILED DESCRIPTION OF THE INVENTION

The NHPs described for the first time herein are novel proteins that may be expressed in, inter alia, human cell lines, human fetal brain, brain, pituitary, cerebellum, spinal cord, thymus, spleen, lymph node, bone marrow, trachea, kidney, fetal liver, prostate, testis, thyroid, adrenal gland, stomach, small intestine, colon, skeletal muscle, uterus, placenta, adipose, esophagus, cervix, rectum, pericardium, fetal kidney, and gene trapped cells.

More particularly, the NHPs that are similar to semaphorins and described for the first time herein in SEQ ID NOS: 1–5, are novel proteins that are expressed in, inter alia, human cell lines, human fetal brain, brain, cerebellum, thymus, spleen, lymph node, kidney, uterus, adipose, esophagus, cervix, rectum, pericardium, placenta, and gene trapped human cells. The NHP described for the first time herein in SEQ ID NOS:6–7 are a novel protein that is expressed in, inter alia, human fetal brain, brain, pituitary, cerebellum, spinal cord, thymus, spleen, lymph node, bone marrow, trachea, kidney, fetal liver, prostate, testis, thyroid, adrenal gland, stomach, small intestine, colon, skeletal muscle, adipose, esophagus, and gene trapped human cell lines. The NHP described for the first time herein in SEQ ID NOS:8–10 is a novel protein that is expressed in, inter alia, human fetal brain, brain, cerebellum, thymus, kidney, fetal liver, prostate, skeletal muscle, esophagus, rectum, pericardium, fetal kidney and gene trapped human cell lines.

The present invention encompasses the nucleotides presented in the Sequence Listing, host cells expressing such nucleotides, the expression products of such nucleotides, and: (a) nucleotides that encode mammalian homologs of the described polynucleotides, including the specifically described NHPs, and the NHP products; (b) nucleotides that encode one or more portions of the NHPs that correspond to functional domains, and the polypeptide products specified by such nucleotide sequences, including but not limited to the novel regions of any active domain(s); (c) isolated nucleotides that encode mutant versions, engineered or naturally occurring, of the described NHPs in which all or a part of at least one domain is deleted or altered, and the polypeptide products specified by such nucleotide sequences, including but not limited to soluble proteins and peptides in which all or a portion of the signal (or hydrophobic transmembrane) sequence is deleted; (d) nucleotides that encode chimeric fusion proteins containing all or a portion of a coding region of an NHP, or one of its domains (e.g., a receptor or ligand binding domain, accessory protein/self-association domain, etc.) fused to another peptide or polypeptide; or (e) therapeutic or diagnostic derivatives of the described polynucleotides such as oligonucleotides, antisense polynucleotides, ribozymes, dsRNA, or gene therapy constructs comprising a sequence first disclosed in the Sequence Listing. As discussed above, the present invention includes: (a) the human DNA sequences presented in the Sequence Listing (and vectors comprising the same) and additionally contemplates any nucleotide sequence encoding a contiguous NHP open reading frame (ORF) that hybridizes to a complement of a DNA sequence presented in the Sequence Listing under highly stringent conditions, e.g., hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. (Ausubel F.M. et al., eds., 1989, Current Protocols in Molecular Biology, Vol. I, Green Publishing Associates, Inc., and John Wiley & sons, Inc., New York, at p. 2.10.3, and encodes a functionally equivalent gene product. Additionally contemplated are any nucleotide sequences that hybridize to the complement of a DNA sequence that encodes and expresses an amino acid sequence presented in the Sequence Listing under moderately stringent conditions, e.g., washing in 0.2×SSC/0.1% SDS at 42° C. (Ausubel et al., 1989, supra), yet still encodes a functionally equivalent NHP product. Functional equivalents of a NHP include naturally occurring NHPs present in other species and mutant NHPs whether naturally occurring or engineered (by site directed mutagenesis, gene shuffling, directed evolution as described in, for example, U.S. Pat. No. 5,837,458). The invention also includes degenerate nucleic acid variants of the disclosed NHP polynucleotide sequences.

Additionally contemplated are polynucleotides encoding NHP ORFs, or their functional equivalents, encoded by polynucleotide sequences that are about 99, 95, 90, or about 85 percent similar or identical to corresponding regions of the nucleotide sequences of the Sequence Listing (as measured by BLAST sequence comparison analysis using, for example, the GCG sequence analysis package using standard default settings).

The invention also includes nucleic acid molecules, preferably DNA molecules, that hybridize to, and are therefore the complements of, the described NHP nucleotide sequences. Such hybridization conditions may be highly stringent or less highly stringent, as described above. In instances where the nucleic acid molecules are deoxyoligonucleotides ("DNA oligos"), such molecules are generally about 16 to about 100 bases long, or about 20 to about 80, or about 34 to about 45 bases long, or any variation or combination of sizes represented therein that incorporate a contiguous region of sequence first disclosed in the Sequence Listing. Such oligonucleotides can be used in conjunction with the polymerase chain reaction (PCR) to screen libraries, isolate clones, and prepare cloning and sequencing templates, etc.

Alternatively, such NHP oligonucleotides can be used as hybridization probes for screening libraries, and assessing gene expression patterns (particularly using a micro array or high-throughput "chip" format). Additionally, a series of the described NHP oligonucleotide sequences, or the complements thereof, can be used to represent all or a portion of the described NHP sequences. An oligonucleotide or polynucleotide sequence first disclosed in at least a portion of one or more of the sequences of SEQ ID NOS: 1–10 can be used as a hybridization probe in conjunction with a solid support matrix/substrate (resins, beads, membranes, plastics, polymers, metal or metallized substrates, crystalline or polycrystalline substrates, etc.). Of particular note are spatially addressable arrays (i.e., gene chips, microtiter plates, etc.) of oligonucleotides and polynucleotides, or corresponding oligopeptides and polypeptides, wherein at least one of the biopolymers present on the spatially addressable array comprises an oligonucleotide or polynucleotide sequence first disclosed in at least one of the sequences of SEQ ID NOS: 1–10, or an amino acid sequence encoded thereby. Methods for attaching biopolymers to, or synthesizing biopolymers on, solid support matrices, and conducting binding studies thereon are disclosed in, inter alia, U.S. Pat. Nos. 5,700,637, 5,556,752, 5,744,305, 4,631,211, 5,445,934, 5,252,743, 4,713,326, 5,424,186, and 4,689,405 the disclosures of which are herein incorporated by reference in their entirety.

Addressable arrays comprising sequences first disclosed in SEQ ID NOS:1–10 can be used to identify and characterize the temporal and tissue specific expression of a gene. These addressable arrays incorporate oligonucleotide sequences of sufficient length to confer the required specificity, yet be within the limitations of the production technology. The length of these probes is within a range of between about 8 to about 2000 nucleotides. Preferably the probes consist of 60 nucleotides and more preferably 25 nucleotides from the sequences first disclosed in SEQ ID NOS:1–10.

For example, a series of the described oligonucleotide sequences, or the complements thereof, can be used in chip format to represent all or a portion of the described sequences. The oligonucleotides, typically between about 16 to about 40 (or any whole number within the stated range) nucleotides in length can partially overlap each other and/or the sequence may be represented using oligonucleotides that do not overlap. Accordingly, the described polynucleotide sequences shall typically comprise at least about two or three distinct oligonucleotide sequences of at least about 8 nucleotides in length that are each first disclosed in the described Sequence Listing. Such oligonucleotide sequences can begin at any nucleotide present within a sequence in the Sequence Listing and proceed in either a sense (5'-to-3') orientation vis-a-vis the described sequence or in an antisense orientation.

Microarray-based analysis allows the discovery of broad patterns of genetic activity, providing new understanding of gene functions and generating novel and unexpected insight into transcriptional processes and biological mechanisms. The use of addressable arrays comprising sequences first disclosed in SEQ ID NOS:1–10 provides detailed information about transcriptional changes involved in a specific pathway, potentially leading to the identification of novel components or gene functions that manifest themselves as novel phenotypes.

Probes consisting of sequences first disclosed in SEQ ID NOS:1–10 can also be used in the identification, selection and validation of novel molecular targets for drug discovery. The use of these unique sequences permits the direct confirmation of drug targets and recognition of drug dependent changes in gene expression that are modulated through pathways distinct from the drugs intended target. These unique sequences therefore also have utility in defining and monitoring both drug action and toxicity.

As an example of utility, the sequences first disclosed in SEQ ID NOS:1–10 can be utilized in microarrays or other assay formats, to screen collections of genetic material from patients who have a particular medical condition. These investigations can also be carried out using the sequences first disclosed in SEQ ID NOS:1–10 in silico and by comparing previously collected genetic databases and the disclosed sequences using computer software known to those in the art.

Thus the sequences first disclosed in SEQ ID NOS:1–10 can be used to identify mutations associated with a particular disease and also as a diagnostic or prognostic assay.

Although the presently described sequences have been specifically described using nucleotide sequence, it should be appreciated that each of the sequences can uniquely be described using any of a wide variety of additional structural attributes, or combinations thereof. For example, a given sequence can be described by the net composition of the nucleotides present within a given region of the sequence in conjunction with the presence of one or more specific oligonucleotide sequence(s) first disclosed in the SEQ ID NOS: 1–10. Alternatively, a restriction map specifying the relative positions of restriction endonuclease digestion sites, or various palindromic or other specific oligonucleotide sequences can be used to structurally describe a given sequence. Such restriction maps, which are typically generated by widely available computer programs (e.g., the University of Wisconsin GCG sequence analysis package, SEQUENCHER 3.0, Gene Codes Corp., Ann Arbor, Mich., etc.), can optionally be used in conjunction with one or more discrete nucleotide sequence(s) present in the sequence that can be described by the relative position of the sequence relatve to one or more additional sequence(s) or one or more restriction sites present in the disclosed sequence.

For oligonucleotide probes, highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as NHP gene antisense molecules, useful, for example, in NHP gene regulation (for and/or as antisense primers in amplification reactions of NHP gene nucleic acid sequences). With respect to NHP gene regulation, such techniques can be used to regulate biological functions. Further, such sequences may be used as part of ribozyme and/or triple helix sequences that are also useful for NHP gene regulation.

Inhibitory antisense or double stranded oligonucleotides can additionally comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide can also comprise at least one modified sugar moiety selected from the group including but not limited to arabinose, 2-fluoroarabinose, xylulose, and hexose.

In yet another embodiment, the antisense oligonucleotide will comprise at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330). Alternatively, double stranded RNA can be used to disrupt the expression and function of a targeted NHP.

Oligonucleotides of the invention can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al. (1988, Nucl. Acids Res. 16:3209), and methylphosphonate oligonucleotides can be prepared by use of controlled pore glass polymer supports (Sarin et al., 1988, Proc. Natl. Acad. Sci. U.S.A. 85:7448–7451), etc.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual (and periodic updates thereof), Cold Springs Harbor Press, N.Y.; and Ausubel et al., 1989, Current Protocols in Molecular Biology, Green Publishing Associates and Wiley Interscience, N.Y.

Alternatively, suitably labeled NHP nucleotide probes can be used to screen a human genomic library using appropriately stringent conditions or by PCR. The identification and characterization of human genomic clones is helpful for identifying polymorphisms (including, but not limited to, nucleotide repeats, microsatellite alleles, single nucleotide polymorphisms, or coding single nucleotide polymorphisms), determining the genomic structure of a given locus/allele, and designing diagnostic tests. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in diagnostics and pharmacogenomics.

Further, a NHP gene homolog can be isolated from nucleic acid from an organism of interest by performing PCR using two degenerate or "wobble" oligonucleotide primer pools designed on the basis of amino acid sequences within the NHP products disclosed herein. The template for the reaction may be total RNA, mRNA, and/or cDNA obtained by reverse transcription of mRNA prepared from human or non-human cell lines or tissue known or suspected to express an allele of a NHP gene.

The PCR product can be subcloned and sequenced to ensure that the amplified sequences represent the sequence of the desired NHP gene. The PCR fragment can then be used to isolate a full length cDNA clone by a variety of methods. For example, the amplified fragment can be labeled and used to screen a cDNA library, such as a bacteriophage cDNA library. Alternatively, the labeled fragment can be used to isolate genomic clones via the screening of a genomic library.

PCR technology can also be used to isolate full length cDNA sequences. For example, RNA can be isolated, following standard procedures, from an appropriate cellular or tissue source (i.e., one known, or suspected, to express a NHP gene). A reverse transcription (RT) reaction can be performed on the RNA using an oligonucleotide primer specific for the most 5' end of the amplified fragment for the priming of first strand synthesis. The resulting RNA/DNA hybrid may then be "tailed" using a standard terminal transferase reaction, the hybrid may be digested with RNase H, and second strand synthesis may then be primed with a complementary primer. Thus, cDNA sequences upstream of the amplified fragment can be isolated. For a review of cloning strategies that can be used, see e.g., Sambrook et al., 1989, supra.

A cDNA encoding a mutant NHP gene can be isolated, for example, by using PCR. In this case, the first cDNA strand may be synthesized by hybridizing an oligo-dT oligonucleotide to mRNA isolated from tissue known or suspected to be expressed in an individual putatively carrying a mutant NHP allele, and by extending the new strand with reverse transcriptase. The second strand of the cDNA is then synthesized using an oligonucleotide that hybridizes specifically to the 5' end of the normal gene. Using these two primers, the product is then amplified via PCR, optionally cloned into a suitable vector, and subjected to DNA sequence analysis through methods well known to those of skill in the art. By comparing the DNA sequence of the mutant NHP allele to that of a corresponding normal NHP allele, the mutation(s) responsible for the loss or alteration of function of the mutant NHP gene product can be ascertained.

Alternatively, a genomic library can be constructed using DNA obtained from an individual suspected of or known to carry a mutant NHP allele (e.g., a person manifesting a NHP-associated phenotype such as, for example, obesity, high blood pressure, connective tissue disorders, infertility, etc.), or a cDNA library can be constructed using RNA from a tissue known, or suspected, to express a mutant NHP allele. A normal NHP gene, or any suitable fragment thereof, can then be labeled and used as a probe to identify the corresponding mutant NHP allele in such libraries. Clones containing mutant NHP gene sequences can then be purified and subjected to sequence analysis according to methods well known to those skilled in the art.

Additionally, an expression library can be constructed utilizing cDNA synthesized from, for example, RNA isolated from a tissue known, or suspected, to express a mutant NHP allele in an individual suspected of or known to carry such a mutant allele. In this manner, gene products made by the putatively mutant tissue can be expressed and screened using standard antibody screening techniques in conjunction with antibodies raised against a normal NHP product, as described below. (For screening techniques, see, for example, Harlow, E. and Lane, eds., 1988, "Antibodies: A Laboratory Manual", Cold Spring Harbor Press, Cold Spring Harbor, N.Y.).

Additionally, screening can be accomplished by screening with labeled NHP fusion proteins, such as, for example, alkaline phosphatase-NHP or NHP-alkaline phosphatase fusion proteins. In cases where a NHP mutation results in an expressed gene product with altered function (e.g. , as a result of a missense or a frameshift mutation), polyclonal antibodies to a NHP are likely to cross-react with a corresponding mutant NHP gene product. Library clones detected via their reaction with such labeled antibodies can be purified and subjected to sequence analysis according to methods well known in the art.

The invention also encompasses (a) DNA vectors that contain any of the foregoing NHP coding sequences and/or their complements (i.e., antisense); (b) DNA expression vectors that contain any of the foregoing NHP coding sequences operatively associated with a regulatory element that directs the expression of the coding sequences (for example, baculo virus as described in U.S. Pat. No. 5,869,336 herein incorporated by reference); (c) genetically engineered host cells that contain any of the foregoing NHP coding sequences operatively associated with a regulatory element that directs the expression of the coding sequences in the host cell; and (d) genetically engineered host cells that express an endogenous NHP gene under the control of an exogenously introduced regulatory element (i.e., gene activation). As used herein, regulatory elements include, but are not limited to, inducible and non-inducible promoters, enhancers, operators and other elements known to those skilled in the art that drive and regulate expression. Such regulatory elements include but are not limited to the cytomegalovirus (hCMV) immediate early gene, regulatable, viral elements (particularly retroviral LTR promoters), the early or late promoters of SV40 adenovirus, the lac system, the trp system, the TAC system, the TRC system, the major operator and promoter regions of phage lambda, the control regions of fd coat protein, the promoter for 3-phosphoglycerate kinase (PGK), the promoters of acid phosphatase, and the promoters of the yeast α-mating factors.

The present invention also encompasses antibodies and anti-idiotypic antibodies (including Fab fragments), antagonists and agonists of the NHP, as well as compounds or nucleotide constructs that inhibit expression of a NHP gene (transcription factor inhibitors, antisense and ribozyme molecules, or gene or regulatory sequence replacement constructs), or promote the expression of a NHP (e.g., expression constructs in which NHP coding sequences are operatively associated with expression control elements such as promoters, promoter/enhancers, etc.).

The NHPs or NHP peptides, NHP fusion proteins, NHP nucleotide sequences, antibodies, antagonists and agonists can be useful for the detection of mutant NHPs or inappropriately expressed NHPs for the diagnosis of disease. The NHP proteins or peptides, NHP fusion proteins, NHP nucleotide sequences, host cell expression systems, antibodies, antagonists, agonists and genetically engineered cells and animals can be used for screening for drugs (or high throughput screening of combinatorial libraries) effective in the treatment of the symptomatic or phenotypic manifestations of perturbing the normal function of NHP in the body. The use of engineered host cells and/or animals may offer an advantage in that such systems allow not only for the identification of compounds that bind to the endogenous receptor for an NHP, but can also identify compounds that trigger NHP-mediated activities or pathways.

Finally, the NHP products can be used as therapeutics. For example, soluble derivatives such as NHP peptides/domains corresponding to NHPs, NHP fusion protein products (especially NHP-Ig fusion proteins, i.e., fusions of a NHP, or a domain of a NHP, to an IgFc), NHP antibodies and anti-idiotypic antibodies (including Fab fragments), antagonists or agonists (including compounds that modulate or act on downstream targets in a NHP-mediated pathway) can be used to directly treat diseases or disorders. For instance, the administration of an effective amount of soluble NHP, or a NHP-IgFc fusion protein or an anti-idiotypic antibody (or its Fab) that mimics the NHP could activate or effectively antagonize the endogenous NHP receptor. Nucleotide constructs encoding such NHP products can be used to genetically engineer host cells to express such products in vivo; these genetically engineered cells function as "bioreactors" in the body delivering a continuous supply of a NHP, a NHP peptide, or a NHP fusion protein to the body. Nucleotide constructs encoding functional NHPs, mutant NHPs, as well as antisense and ribozyme molecules can also be used in "gene therapy" approaches for the modulation of NHP expression. Thus, the invention also encompasses pharmaceutical formulations and methods for treating biological disorders.

Various aspects of the invention are described in greater detail in the subsections below.

The Nhp Sequences

The cDNA sequences and the corresponding deduced amino acid sequences of the described NHPs are presented in the Sequence Listing. The NHP nucleotides described in SEQ ID NOS:1–5 were obtained from clustered human gene trapped sequences, ESTs, and cDNA isolated from a human placenta cDNA cell library (Edge Biosystems, Gaithersburg, Md.).

The sequences described in SEQ ID NOS:1–5 share limited structural similarity with a variety of proteins, including, but not limited to, semaphorins and collapsing. A polymorphism was identified that results in a translationally silent A-to-G transition at, for example, the position corresponding to nucleotide 2106 of SEQ ID NO:1. Because of their role in neural development, semaphorins have been subject to considerable scientific scrutiny. For example, U.S. Patents Nos. 5,981,222 and 5,935,865, both of which are herein incorporated by reference, describe other semaphorins as well as applications, utilities, and uses that also pertain to the described semphorin-like NHPs.

The cDNA sequence (SEQ ID NO: 6) and the corresponding deduced amino acid sequence (SEQ ID NO: 7) presented in the Sequence Listing were obtained by analyzing human gene trapped sequence tags. The "m" at position 124 of SEQ ID NO:6 represents an A-or-C polymorphism that can result in either a S or a R (preferred) at corresponding amino acid position 42 of SEQ ID NO:7, and the "y" displayed at position 233 of SEQ ID NO:6 represents a C-or-T polymorphism that can result in either a T or a M at corresponding amino acid position 158 of SEQ ID NO:7. The sequences described in SEQ ID NOS:6–7 share limited structural similarity with a variety of proteins, including, but not limited to, protein/peptide hormones of the neurohypophysial family.

The cDNA sequence (SEQ ID NO: 8) and the corresponding deduced amino acid sequence (SEQ ID NO: 9) were obtained by analyzing human gene trapped sequence tags and cDNA clones isolated from a human kidney cDNA library (Edge Biosystems, Gaithersburg, Md.). The sequences described in SEQ ID NOS:8–10 share limited structural similarity with a variety of proteins, including, but not limited to, protein/peptide hormones of the oxytocin (neurophysin 1 precursor) family.

Nhps and Nhp Polypeptides

NHPs, polypeptides, peptide fragments, mutated, truncated, or deleted forms of the NHPs, and/or NHP fusion proteins can be prepared for a variety of uses. These uses include but are not limited to the generation of antibodies, as reagents in diagnostic assays, the identification of other cellular gene products related to a NHP, as reagents in assays for screening for compounds that can be as pharmaceutical reagents useful in the therapeutic treatment of mental, biological, or medical disorders and diseases. Given the similarity information and expression data, the described NHPs can be targeted (by drugs, oligos, antibodies, etc,) in order to treat disease, or to therapeutically augment the efficacy of, for example, chemotherapeutic agents used in the treatment of breast or prostate cancer.

The Sequence Listing discloses the amino acid sequences encoded by the described NHP polynucleotides. The NHPs typically display have initiator methionines in DNA sequence contexts consistent with a translation initiation site.

The NHP amino acid sequences of the invention include the amino acid sequence presented in the Sequence Listing as well as analogues and derivatives thereof. Further, corresponding NHP homologues from other species are encompassed by the invention. In fact, any NHP protein encoded by the NHP nucleotide sequences described above are within the scope of the invention, as are any novel polynucleotide sequences encoding all or any novel portion of an amino acid sequence presented in the Sequence Listing. The degenerate nature of the genetic code is well known, and, accordingly, each amino acid presented in the Sequence Listing, is generically representative of the well known nucleic acid "triplet" codon, or in many cases codons, that can encode the amino acid. As such, as contemplated herein, the amino acid sequences presented in the Sequence Listing, when taken together with the genetic code (see, for example, Table 4-1 at page 109 of "Molecular Cell Biology", 1986, J. Darnell et al. eds., Scientific American Books, New York, N.Y., herein incorporated by reference) are generically representative of all the various permutations and combinations of nucleic acid sequences that can encode such amino acid sequences.

The invention also encompasses proteins that are functionally equivalent to the NHPs encoded by the presently described nucleotide sequences as judged by any of a number of criteria, including, but not limited to, the ability to bind and cleave a substrate of a NHP, or the ability to effect an identical or complementary downstream pathway, or a change in cellular metabolism (e.g., proteolytic activity, ion flux, tyrosine phosphorylation, etc.). Such functionally equivalent NHP proteins include, but are not limited to, additions or substitutions of amino acid residues within the amino acid sequence encoded by the NHP nucleotide sequences described above, but which result in a silent change, thus producing a functionally equivalent gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

A variety of host-expression vector systems can be used to express the NHP nucleotide sequences of the invention. Where, as in the present instance, the NHP peptide or polypeptide is thought to be membrane protein, the hydrophobic regions of the protein can be excised and the resulting soluble peptide or polypeptide can be recovered from the culture media. Such expression systems also encompass engineered host cells that express a NHP, or functional equivalent, in situ. Purification or enrichment of a NHP from such expression systems can be accomplished using appropriate detergents and lipid micelles and methods well known to those skilled in the art. However, such engineered host cells themselves may be used in situations where it is important not only to retain the structural and functional characteristics of the NHP, but to assess biological activity, e.g., in drug screening assays.

The expression systems that may be used for purposes of the invention include but are not limited to microorganisms such as bacteria (e.g., *E. coli, B. subtilis*) transformed with recombinant bacteriophage DNA, plasmid DNA or cosmid DNA expression vectors containing NHP nucleotide sequences; yeast (e.g., Saccharomyces, Pichia) transformed with recombinant yeast expression vectors containing NHP nucleotide sequences; insect cell systems infected with recombinant virus expression vectors (e.g., baculovirus) containing NHP sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing NHP nucleotide sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the NHP product being expressed. For example, when a large quantity of such a protein is to be produced for the generation of pharmaceutical compositions of or containing NHP, or for raising antibodies to a NHP, vectors that direct the expression of high levels of fusion protein products that are readily purified may be desirable. Such vectors include, but are not limited, to the *E. coli* expression vector pUR278 (Ruther et al., 1983, EMBO J. 2:1791), in which a NHP coding sequence may be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors (Pharmacia or American Type Culture Collection) can also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

In an insect system, *Autographa californica* nuclear polyhidrosis virus (AcNPV) is used as a vector to express foreign genes. The virus grows in *Spodoptera frugiperda* cells. A NHP coding sequence may be cloned individually into non-essential regions (for example the polyhedrin gene) of the virus and placed under control of an AcNPV promoter (for example the polyhedrin promoter). Successful insertion of NHP coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted sequence is expressed (e.g., see Smith et al., 1983, J. Virol. 46:584; Smith, U.S. Pat. No. 4,215,051).

In mammalian host cells, a number of viral-based expression systems may be utilized. In cases where an adenovirus is used as an expression vector, the NHP nucleotide sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing a NHP product in infected hosts (e.g., See Logan & Shenk, 1984, Proc. Natl. Acad. Sci. USA 81:3655–3659). Specific initiation signals may also be required for efficient translation of inserted NHP nucleotide sequences. These signals include the ATG initiation codon and adjacent sequences. In cases where an entire NHP gene or cDNA, including its own initiation codon and adjacent sequences, is inserted into the appropriate expression vector, no additional translational control signals may be needed. However, in cases where only a portion of a NHP coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bitter et al., 1987, Methods in Enzymol. 153:516–544).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERO, BHK, HeLa, COS, MDCK, 293, 3T3, WI38, and in particular, human cell lines.

For long-term, high-yield production of recombinant proteins, stable expression is preferred. For example, cell lines which stably express the NHP sequences described above can be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the NHP product. Such engineered cell lines may be particularly useful in screening and evaluation of compounds that affect the endogenous activity of the NHP product.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk$^-$, hgprt$^-$ or aprt$^-$ cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, any fusion protein can be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88:8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto Ni$^{2+}$ nitriloacetic acid-agarose columns and histidine-tagged proteins are selectively eluted with imidazole-containing buffers.

Also encompassed by the present invention are fusion proteins that direct the NHP to a target organ and/or facilitate transport across the membrane into the cytosol. Conjugation of NHPs to antibody molecules or their Fab fragments could be used to target cells bearing a particular epitope. Attaching the appropriate signal sequence to the NHP would also transport the NHP to the desired location within the cell. Alternatively targeting of NHP or its nucleic acid sequence might be achieved using liposome or lipid complex based delivery systems. Such technologies are described in *Liposomes:A Practical Approach,* New, RRC ed., Oxford University Press, New York and in U.S. Pat. Nos. 4,594,595, 5,459,127, 5,948,767 and 6,110,490 and their respective disclosures which are herein incorporated by reference in their entirety. Additionally embodied are novel protein constructs engineered in such a way that they facilitate transport of the NHP to the target site or desired organ. This goal may be achieved by coupling of the NHP to a cytokine or other ligand that provides targeting specificity, and/or to a protein transducing domain (see generally U.S. applications Ser. Nos. 60/111,701 and 60/056,713, both of which are herein incorporated by reference, for examples of such transducing sequences) to facilitate passage across cellular membranes if needed and can optionally be engineered to include nuclear localization sequences when desired.

Antibodies to NHP Products

Antibodies that specifically recognize one or more epitopes of a NHP, or epitopes of conserved variants of a NHP, or peptide fragments of a NHP are also encompassed by the invention. Such antibodies include but are not limited to polyclonal antibodies, monoclonal antibodies (mAbs), humanized or chimeric antibodies, single chain antibodies, Fab fragments, $F(ab')_2$ fragments, fragments produced by a Fab expression library, anti-idiotypic (anti-Id) antibodies, and epitope-binding fragments of any of the above.

The antibodies of the invention may be used, for example, in the detection of NHP in a biological sample and may, therefore, be utilized as part of a diagnostic or prognostic technique whereby patients may be tested for abnormal amounts of NHP. Such antibodies may also be utilized in conjunction with, for example, compound screening schemes for the evaluation of the effect of test compounds on expression and/or activity of a NHP gene product. Additionally, such antibodies can be used in conjunction gene therapy to, for example, evaluate the normal and/or engineered NHP-expressing cells prior to their introduction into the patient. Such antibodies may additionally be used as a method for the inhibition of abnormal NHP activity. Thus, such antibodies may, therefore, be utilized as part of treatment methods.

For the production of antibodies, various host animals may be immunized by injection with a NHP, an NHP peptide (e.g., one corresponding to a functional domain of an NHP), truncated NHP polypeptides (NHP in which one or more domains have been deleted), functional equivalents of the NHP or mutated variant of the NHP. Such host animals may include but are not limited to pigs, rabbits, mice, goats, and rats, to name but a few. Various adjuvants may be used to increase the immunological response, depending on the host species, including but not limited to Freund's adjuvant (complete and incomplete), mineral salts such as aluminum hydroxide or aluminum phosphate, surface active substances such as lysolecithin, pluronic polyols, polyanions, peptides, oil emulsions, and potentially useful human adjuvants such as BCG (bacille Calmette-Guerin) and *Corynebacterium parvum.* Alternatively, the immune response could be enhanced by combination and or coupling with molecules such as keyhole limpet hemocyanin, tetanus toxoid, diptheria toxoid, ovalbumin, cholera toxin or fragments thereof. Polyclonal antibodies are heterogeneous populations of antibody molecules derived from the sera of the immunized animals.

Monoclonal antibodies, which are homogeneous populations of antibodies to a particular antigen, can be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mabs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. Such technologies are described in U.S. Pat. Nos. 6,075,181 and 5,877,397 and their respective disclosures which are herein incorporated by reference in their entirety. Also encompassed by the present invention is the use of fully humanized monoclonal antibodies as described in US Pat. No. 6,150,584 and respective disclosures which are herein incorporated by reference in their entirety.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 341:544–546) can be adapted to produce single chain antibodies against NHP gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include, but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al. , 1989, Science, 246:1275–1281) to allow rapid and easy identification of monoclonal Fab fragments with the desired specificity.

Antibodies to a NHP can, in turn, be utilized to generate anti-idiotype antibodies that "mimic" a given NHP, using techniques well known to those skilled in the art. (See, e.g., Greenspan & Bona, 1993, FASEB J 7(5):437–444; and Nissinoff, 1991, J. Immunol. 147(8):2429–2438). For example antibodies which bind to a NHP domain and competitively inhibit the binding of NHP to its cognate receptor can be used to generate anti-idiotypes that "mimic" the NHP and, therefore, bind and activate or neutralize a receptor. Such anti-idiotypic antibodies or Fab fragments of such anti-idiotypes can be used in therapeutic regimens involving a NHP mediated pathway.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art form the foregoing description. Such modifications are intended to fall within the scope of the appended claims. All cited publications, patents, and patent applications are here incorporated by reference in their entirety.

What is claimed is:

1. An isolated nucleic acid molecule comprising the nucleotide sequence of SEQ ID NO: 1.

2. An isolated nucleic acid molecule comprising a nucleotide sequence that:
   (a) encodes the amino acid sequence shown in SEQ ID NO: 2; and
   (b) hybridizes under stringent conditions to the complement nucleotide sequence of SEQ ID NO: 1.

3. An isolated nucleic acid molecule comprising a nucleotide sequence that encodes the amino acid sequence shown in SEQ ID NO: 2.

4. An isolated nucleic acid molecule comprising a nucleotide sequence that encodes the amino acid sequence shown in SEQ ID NO:4.

5. An expression vector comprising the nucleic acid sequence of claim 4.

6. A cell comprising the expression vector of claim 5.

* * * * *

SEQUENCE LISTING

<160> NUMBER OF SEQ ID NOS: 10

<210> SEQ ID NO 1
<211> LENGTH: 2628
<212> TYPE: DNA
<213> ORGANISM: homo sapiens

<400> SEQUENCE: 1

```
atggcctgtg ccctagctgg gaaggtcttc ccaatgggga gctggccagt gtggcacaaa      60
agcctgcact gggccaacaa ggtggaagga gaagcggcag gtggacggca aggccccagc     120
ctccttctct cctccgcccc tcttcccgcc caggactggg tggagccact gccttataag     180
tggtggcctg gtggcagcag agcaaactac aaccggcggc cagcgggacc agagggcggc     240
tctgcaggca ggcggcagcg gtgccctcag ttccccagca tggcccctc ggcctgggcc      300 atttgctggc tgctagggggg cctcctgctc catggggta gctctggccc cagcccggc      360 cccagtgtgc cccgcctgcg gctctcctac cgagacctcc tgtctgccaa ccgctctgcc     420
atctttctgg gccccaggg ctccctgaac ctccaggcca tgtacctaga tgagtaccga     480
gaccgcctct ttctgggtgg cctggacgcc ctctactctc tgcggctgga ccaggcatgg     540
ccagatcccc gggaggtcct gtggccaccg cagccaggac agagggagga gtgtgttcga     600
aagggaagag atcctttgac agagtgcgcc aacttcgtgc gggtgctaca gcctcacaac     660
```

| | |
|---|---|
| cggacccacc tgctagcctg tggcactggg gccttccagc ccacctgtgc cctcatcaca | 720 |
| gttggccacc gtggggagca tgtgctccac ctggagcctg gcagtgtgga aagtggccgg | 780 |
| gggcggtgcc ctcacgagcc cagccgtccc tttgccagca ccttcataga cggggagctg | 840 |
| tacacgggtc tcactgctga cttcctgggg cgagaggcca tgatcttccg aagtggaggt | 900 |
| cctcggccag ctctgcgttc cgactctgac cagagtctct tgcacgaccc ccggtttgtg | 960 |
| atggccgccc ggatccctga aactctgaca caggacaatg acaaggtgta cttcttcttc | 1020 |
| tcggagacgg tccccctcgcc cgatggtggc tcgaaccatg tcactgtcag ccgcgtgggc | 1080 |
| cgcgtctgcg tgaatgatgc tgggggccag cgggtgctgg tgaacaaatg gagcactttc | 1140 |
| ctcaaggcca ggctggtctg ctcggtgccc ggccctggtg gtgccgagac ccactttgac | 1200 |
| cagctagagg atgtgttcct gctgtggccc aaggccggga gagcctcga ggtgtacgcg | 1260 |
| ctgttcagca ccgtcagtgc cgtgttccag ggcttcgccg tctgtgtgta ccacatggca | 1320 |
| gacatctggg aggttttcaa cgggcccttt gcccaccgag atgggcctca gcaccagtgg | 1380 |
| gggccctatg ggggcaaggt gcccttccct cgccctggcg tgtgccccag caagatgacc | 1440 |
| gcacagccag gacggccttt tggcagcacc aaggactacc cagatgaggt gctgcagttt | 1500 |
| gcccgagccc accccctcat gttctggcct gtgcggcctc gacatggccg ccctgtcctt | 1560 |
| gtcaagaccc acctggccca gcagctacac cagatcgtgg tggaccgcgt ggaggcagag | 1620 |
| gatgggacct acgatgtcat tttcctgggg actgactcag ggtctgtgct caaagtcatc | 1680 |
| gctctccagg caggggggctc agctgaacct gaggaagtgg ttctggagga gctccaggtg | 1740 |
| tttaaggtgc caacacctat caccgaaatg gagatctctg tcaaaaggca aatgctatac | 1800 |
| gtgggctctc ggctggtgtg ggcccagctg cggctgcacc aatgtgagac ttacggcact | 1860 |
| gcctgtgcag agtgctgcct ggcccgggac ccatactgtg cctgggatgg tgcctcctgt | 1920 |
| acccactacc gccccagcct tggcaagcgc cggttccgcc ggcaggacat ccggcacggc | 1980 |
| aaccctgccc tgcagtgcct gggccagagc caggaagaag aggcagtggg acttgtggca | 2040 |
| gccaccatgg tctacggcac ggagcacaat agcaccttcc tggagtgcct gcccaagtct | 2100 |
| ccccargctg ctgtgcgctg gctcttgcag aggccagggg atgaggggcc tgaccaggtg | 2160 |
| aagacggacg agcgagtctt gcacacggag cgggggctgc tgttccgcag gcttagccgt | 2220 |
| ttcgatgcgg gcacctacac ctgcaccact ctggagcatg gcttctccca gactgtggtc | 2280 |
| cgcctggctc tggtggtgat tgtggcctca cagctggaca acctgttccc tccggagcca | 2340 |
| aagccagagg agcccccagc ccggggaggc ctggcttcca ccccacccaa ggcctggtac | 2400 |
| aaggacatcc tgcagctcat tggcttcgcc aacctgcccc gggtggatga gtactgtgag | 2460 |
| cgcgtgtggt gcagggcac cacgaatgc tcaggctgct tccggagccg gagccggggc | 2520 |
| aagcaggcca ggggcaagag ctgggcaggg ctggagctag caagaagat gaagagccgg | 2580 |
| gtgcatgcca agcacaatcg gacgccccgg gaggtggagg ccacgtag | 2628 |

<210> SEQ ID NO 2
<211> LENGTH: 875
<212> TYPE: PRT
<213> ORGANISM: homo sapiens

<400> SEQUENCE: 2

Met Ala Cys Ala Leu Ala Gly Lys Val Phe Pro Met Gly Ser Trp Pro
1               5                   10                  15

Val Trp His Lys Ser Leu His Trp Ala Asn Lys Val Glu Gly Glu Ala
            20                  25                  30

-continued

```
Ala Gly Gly Arg Gln Gly Pro Ser Leu Leu Ser Ser Ala Pro Leu
         35                  40                  45

Pro Ala Gln Asp Trp Val Glu Pro Leu Pro Tyr Lys Trp Trp Pro Gly
 50                  55                  60

Gly Ser Arg Ala Asn Tyr Asn Arg Arg Pro Ala Gly Pro Glu Gly Gly
 65                  70                  75                  80

Ser Ala Gly Arg Arg Gln Arg Cys Pro Gln Phe Pro Ser Met Ala Pro
                 85                  90                  95

Ser Ala Trp Ala Ile Cys Trp Leu Leu Gly Leu Leu Leu His Gly
                100                 105                 110

Gly Ser Ser Gly Pro Ser Pro Gly Pro Ser Val Pro Arg Leu Arg Leu
             115                 120                 125

Ser Tyr Arg Asp Leu Leu Ser Ala Asn Arg Ser Ala Ile Phe Leu Gly
130                 135                 140

Pro Gln Gly Ser Leu Asn Leu Gln Ala Met Tyr Leu Asp Glu Tyr Arg
145                 150                 155                 160

Asp Arg Leu Phe Leu Gly Gly Leu Asp Ala Leu Tyr Ser Leu Arg Leu
                165                 170                 175

Asp Gln Ala Trp Pro Asp Pro Arg Glu Val Leu Trp Pro Pro Gln Pro
            180                 185                 190

Gly Gln Arg Glu Glu Cys Val Arg Lys Gly Arg Asp Pro Leu Thr Glu
            195                 200                 205

Cys Ala Asn Phe Val Arg Val Leu Gln Pro His Asn Arg Thr His Leu
210                 215                 220

Leu Ala Cys Gly Thr Gly Ala Phe Gln Pro Thr Cys Ala Leu Ile Thr
225                 230                 235                 240

Val Gly His Arg Gly Glu His Val Leu His Leu Glu Pro Gly Ser Val
                245                 250                 255

Glu Ser Gly Arg Gly Arg Cys Pro His Glu Pro Ser Arg Pro Phe Ala
            260                 265                 270

Ser Thr Phe Ile Asp Gly Glu Leu Tyr Thr Gly Leu Thr Ala Asp Phe
275                 280                 285

Leu Gly Arg Glu Ala Met Ile Phe Arg Ser Gly Gly Pro Arg Pro Ala
290                 295                 300

Leu Arg Ser Asp Ser Asp Gln Ser Leu Leu His Asp Pro Arg Phe Val
305                 310                 315                 320

Met Ala Ala Arg Ile Pro Glu Asn Ser Asp Gln Asp Asn Asp Lys Val
                325                 330                 335

Tyr Phe Phe Phe Ser Glu Thr Val Pro Ser Pro Asp Gly Gly Ser Asn
            340                 345                 350

His Val Thr Val Ser Arg Val Gly Arg Val Cys Val Asn Asp Ala Gly
            355                 360                 365

Gly Gln Arg Val Leu Val Asn Lys Trp Ser Thr Phe Leu Lys Ala Arg
370                 375                 380

Leu Val Cys Ser Val Pro Gly Pro Gly Gly Ala Glu Thr His Phe Asp
385                 390                 395                 400

Gln Leu Glu Asp Val Phe Leu Leu Trp Pro Lys Ala Gly Lys Ser Leu
                405                 410                 415

Glu Val Tyr Ala Leu Phe Ser Thr Val Ser Ala Val Phe Gln Gly Phe
            420                 425                 430

Ala Val Cys Val Tyr His Met Ala Asp Ile Trp Glu Val Phe Asn Gly
435                 440                 445
```

-continued

```
Pro Phe Ala His Arg Asp Gly Pro Gln His Gln Trp Gly Pro Tyr Gly
    450                 455                 460
Gly Lys Val Pro Phe Pro Arg Pro Gly Val Cys Pro Ser Lys Met Thr
465                 470                 475                 480
Ala Gln Pro Gly Arg Pro Phe Gly Ser Thr Lys Asp Tyr Pro Asp Glu
                485                 490                 495
Val Leu Gln Phe Ala Arg Ala His Pro Leu Met Phe Trp Pro Val Arg
            500                 505                 510
Pro Arg His Gly Arg Pro Val Leu Val Lys Thr His Leu Ala Gln Gln
        515                 520                 525
Leu His Gln Ile Val Val Asp Arg Val Glu Ala Glu Asp Gly Thr Tyr
    530                 535                 540
Asp Val Ile Phe Leu Gly Thr Asp Ser Gly Ser Val Leu Lys Val Ile
545                 550                 555                 560
Ala Leu Gln Ala Gly Gly Ser Ala Glu Pro Glu Val Val Leu Glu
                565                 570                 575
Glu Leu Gln Val Phe Lys Val Pro Thr Pro Ile Thr Glu Met Glu Ile
            580                 585                 590
Ser Val Lys Arg Gln Met Leu Tyr Val Gly Ser Arg Leu Gly Val Ala
    595                 600                 605
Gln Leu Arg Leu His Gln Cys Glu Thr Tyr Gly Thr Ala Cys Ala Glu
    610                 615                 620
Cys Cys Leu Ala Arg Asp Pro Tyr Cys Ala Trp Asp Gly Ala Ser Cys
625                 630                 635                 640
Thr His Tyr Arg Pro Ser Leu Gly Lys Arg Arg Phe Arg Arg Gln Asp
                645                 650                 655
Ile Arg His Gly Asn Pro Ala Leu Gln Cys Leu Gly Gln Ser Gln Glu
            660                 665                 670
Glu Glu Ala Val Gly Leu Val Ala Ala Thr Met Val Tyr Gly Thr Glu
        675                 680                 685
His Asn Ser Thr Phe Leu Glu Cys Leu Pro Lys Ser Pro Gln Ala Ala
    690                 695                 700
Val Arg Trp Leu Leu Gln Arg Pro Gly Asp Glu Gly Pro Asp Gln Val
705                 710                 715                 720
Lys Thr Asp Glu Arg Val Leu His Thr Glu Arg Gly Leu Leu Phe Arg
                725                 730                 735
Arg Leu Ser Arg Phe Asp Ala Gly Thr Tyr Thr Cys Thr Thr Leu Glu
            740                 745                 750
His Gly Phe Ser Gln Thr Val Val Arg Leu Ala Leu Val Ile Val
        755                 760                 765
Ala Ser Gln Leu Asp Asn Leu Phe Pro Glu Pro Lys Pro Glu Glu
    770                 775                 780
Pro Pro Ala Arg Gly Gly Leu Ala Ser Thr Pro Lys Ala Trp Tyr
785                 790                 795                 800
Lys Asp Ile Leu Gln Leu Ile Gly Phe Ala Asn Leu Pro Arg Val Asp
                805                 810                 815
Glu Tyr Cys Glu Arg Val Trp Cys Arg Gly Thr Thr Glu Cys Ser Gly
            820                 825                 830
Cys Phe Arg Ser Arg Ser Arg Gly Lys Gln Ala Arg Gly Lys Ser Trp
        835                 840                 845
```

Ala Gly Leu Glu Leu Gly Lys Lys Met Lys Ser Arg Val His Ala Glu
    850             855             860

His Asn Arg Thr Pro Arg Glu Val Glu Ala Thr
865             870             875

<210> SEQ ID NO 3
<211> LENGTH: 2349
<212> TYPE: DNA
<213> ORGANISM: homo sapiens

<400> SEQUENCE: 3

| | | | | |
|---|---|---|---|---|
| atggccccct | cggcctgggc | catttgctgg | ctgctagggg | gcctcctgct | ccatggggt | 60 |
| agctctggcc | ccagccccgg | ccccagtgtg | ccccgcctgc | ggctctccta | ccgagacctc | 120 |
| ctgtctgcca | accgctctgc | catctttctg | ggccccagg | gctccctgaa | cctccaggcc | 180 |
| atgtacctag | atgagtaccg | agaccgcctc | tttctgggtg | gcctggacgc | cctctactct | 240 |
| ctgcggctgg | accaggcatg | gccagatccc | cgggaggtcc | tgtggccacc | gcagccagga | 300 |
| cagagggagg | agtgtgttcg | aaagggaaga | gatcctttga | cagagtgcgc | caacttcgtg | 360 |
| cgggtgctac | agcctcacaa | ccggacccac | ctgctagcct | gtggcactgg | ggccttccag | 420 |
| cccacctgtg | ccctcatcac | agttggccac | cgtggggagc | atgtgctcca | cctggagcct | 480 |
| ggcagtgtgg | aaagtggccg | gggcggtgc | cctcacgagc | ccagccgtcc | ctttgccagc | 540 |
| accttcatag | acggggagct | gtacacgggt | ctcactgctg | acttcctggg | gcgagaggcc | 600 |
| atgatcttcc | gaagtggagg | tcctcggcca | gtctctgcgt | tccgactctga | ccagagtctc | 660 |
| ttgcacgacc | cccggtttgt | gatggccgcc | cggatccctg | agaactctga | ccaggacaat | 720 |
| gacaaggtgt | acttcttctt | ctcggagacg | gtcccctcgc | ccgatggtgg | ctcgaaccat | 780 |
| gtcactgtca | gccgcgtggg | ccgcgtctgc | gtgaatgatg | ctgggggcca | gcgggtgctg | 840 |
| gtgaacaaat | ggagcacttt | cctcaaggcc | aggctggtct | gctcggtgcc | cggccctggt | 900 |
| ggtgccgaga | cccactttga | ccagctagag | gatgtgttcc | tgctgtggcc | caaggccggg | 960 |
| aagagcctcg | aggtgtacgc | gctgttcagc | accgtcagtg | ccgtgttcca | ggcttcgcc | 1020 |
| gtctgtgtgt | accacatggc | agacatctgg | gaggttttca | cgggcccctt | tgcccaccga | 1080 |
| gatgggcctc | agccaccagtg | gggcccctat | ggggcaagg | tgcccttccc | tcgccctggc | 1140 |
| gtgtgcccca | gcaagatgac | cgcacagcca | ggacggcctt | ttggcagcac | caaggactac | 1200 |
| ccagatgagg | tgctgcagtt | tgcccgagcc | caccccctca | tgttctgcc | tgtgcggcct | 1260 |
| cgacatggcc | gccctgtcct | tgtcaagacc | cacctggccc | agcagctaca | ccagatcgtg | 1320 |
| gtggaccgcg | tggaggcaga | ggatgggacc | tacgatgtca | ttttcctggg | gactgactca | 1380 |
| gggtctgtgc | tcaaagtcat | cgctctccag | gcaggggct | cagctgaacc | tgaggaagtg | 1440 |
| gttctggagg | agctccaggt | gtttaaggtg | ccaacaccta | tcaccgaaat | ggagatctct | 1500 |
| gtcaaaaggc | aaatgctata | cgtgggctct | cggctgggtg | tggcccagct | gcggctgcac | 1560 |
| caatgtgaga | cttacggcac | tgcctgtgca | gagtgctgcc | tggcccggga | cccatactgt | 1620 |
| gcctgggatg | gtgcctcctg | tacccactac | cgccccagcc | ttggcaagcg | ccggttccgc | 1680 |
| cggcaggaca | tccggcacgg | caaccctgcc | ctgcagtgcc | tgggccagag | ccaggaagaa | 1740 |
| gaggcagtgg | gacttgtggc | agccaccatg | gtctacggca | cggagcacaa | tagcaccttc | 1800 |
| ctggagtgcc | tgcccaagtc | tcccargct | gctgtgcgct | ggctcttgca | gaggccaggg | 1860 |
| gatgagggc | ctgaccaggt | gaagacggac | gagcgagtct | tgcacacgga | gcggggctg | 1920 |
| ctgttccgca | ggcttagccg | tttcgatgcg | ggcacctaca | cctgcaccac | tctggagcat | 1980 |

```
ggcttctccc agactgtggt ccgcctggct ctggtggtga ttgtggcctc acagctggac    2040
aacctgttcc ctccggagcc aaagccagag gagcccccag cccggggagg cctggcttcc    2100
accccaccca aggcctggta caaggacatc ctgcagctca ttggcttcgc caacctgccc    2160
cgggtggatg agtactgtga gcgcgtgtgg tgcaggggca ccacggaatg ctcaggctgc    2220
ttccggagcc ggagccgggg caagcaggcc aggggcaaga gctgggcagg gctggagcta    2280
ggcaagaaga tgaagagccg ggtgcatgcc gagcacaatc ggacgccccg ggaggtggag    2340
gccacgtag                                                           2349
```

<210> SEQ ID NO 4
<211> LENGTH: 782
<212> TYPE: PRT
<213> ORGANISM: homo sapiens

<400> SEQUENCE: 4

```
Met Ala Pro Ser Ala Trp Ala Ile Cys Trp Leu Leu Gly Gly Leu Leu
 1               5                  10                  15

Leu His Gly Gly Ser Ser Gly Pro Ser Pro Gly Pro Ser Val Pro Arg
            20                  25                  30

Leu Arg Leu Ser Tyr Arg Asp Leu Leu Ser Ala Asn Arg Ser Ala Ile
        35                  40                  45

Phe Leu Gly Pro Gln Gly Ser Leu Asn Leu Gln Ala Met Tyr Leu Asp
    50                  55                  60

Glu Tyr Arg Asp Arg Leu Phe Leu Gly Gly Leu Asp Ala Leu Tyr Ser
65                  70                  75                  80

Leu Arg Leu Asp Gln Ala Trp Pro Asp Pro Arg Glu Val Leu Trp Pro
                85                  90                  95

Pro Gln Pro Gly Gln Arg Glu Glu Cys Val Arg Lys Gly Arg Asp Pro
            100                 105                 110

Leu Thr Glu Cys Ala Asn Phe Val Arg Val Leu Gln Pro His Asn Arg
        115                 120                 125

Thr His Leu Leu Ala Cys Gly Thr Gly Ala Phe Gln Pro Thr Cys Ala
    130                 135                 140

Leu Ile Thr Val Gly His Arg Gly Glu His Val Leu His Leu Glu Pro
145                 150                 155                 160

Gly Ser Val Glu Ser Gly Arg Gly Arg Cys Pro His Glu Pro Ser Arg
                165                 170                 175

Pro Phe Ala Ser Thr Phe Ile Asp Gly Glu Leu Tyr Thr Gly Leu Thr
            180                 185                 190

Ala Asp Phe Leu Gly Arg Glu Ala Met Ile Phe Arg Ser Gly Gly Pro
        195                 200                 205

Arg Pro Ala Leu Arg Ser Asp Ser Asp Gln Ser Leu Leu His Asp Pro
    210                 215                 220

Arg Phe Val Met Ala Ala Arg Ile Pro Glu Asn Ser Asp Gln Asp Asn
225                 230                 235                 240

Asp Lys Val Tyr Phe Phe Phe Ser Glu Thr Val Pro Ser Pro Asp Gly
                245                 250                 255

Gly Ser Asn His Val Thr Val Ser Arg Val Gly Arg Val Cys Val Asn
            260                 265                 270

Asp Ala Gly Gly Gln Arg Val Leu Val Asn Lys Trp Ser Thr Phe Leu
        275                 280                 285

Lys Ala Arg Leu Val Cys Ser Val Pro Gly Pro Gly Gly Ala Glu Thr
    290                 295                 300
```

-continued

```
His Phe Asp Gln Leu Glu Asp Val Phe Leu Leu Trp Pro Lys Ala Gly
305                 310                 315                 320

Lys Ser Leu Glu Val Tyr Ala Leu Phe Ser Thr Val Ser Ala Val Phe
                325                 330                 335

Gln Gly Phe Ala Val Cys Val Tyr His Met Ala Asp Ile Trp Glu Val
            340                 345                 350

Phe Asn Gly Pro Phe Ala His Arg Asp Gly Pro Gln His Gln Trp Gly
        355                 360                 365

Pro Tyr Gly Gly Lys Val Pro Phe Pro Arg Pro Gly Val Cys Pro Ser
    370                 375                 380

Lys Met Thr Ala Gln Pro Gly Arg Pro Phe Gly Ser Thr Lys Asp Tyr
385                 390                 395                 400

Pro Asp Glu Val Leu Gln Phe Ala Arg Ala His Pro Leu Met Phe Trp
                405                 410                 415

Pro Val Arg Pro Arg His Gly Arg Pro Val Leu Val Lys Thr His Leu
            420                 425                 430

Ala Gln Gln Leu His Gln Ile Val Val Asp Arg Val Glu Ala Glu Asp
                435                 440                 445

Gly Thr Tyr Asp Val Ile Phe Leu Gly Thr Asp Ser Gly Ser Val Leu
            450                 455                 460

Lys Val Ile Ala Leu Gln Ala Gly Gly Ser Ala Glu Pro Glu Glu Val
465                 470                 475                 480

Val Leu Glu Glu Leu Gln Val Phe Lys Val Pro Thr Pro Ile Thr Glu
                485                 490                 495

Met Glu Ile Ser Val Lys Arg Gln Met Leu Tyr Val Gly Ser Arg Leu
            500                 505                 510

Gly Val Ala Gln Leu Arg Leu His Gln Cys Glu Thr Tyr Gly Thr Ala
            515                 520                 525

Cys Ala Glu Cys Cys Leu Ala Arg Asp Pro Tyr Cys Ala Trp Asp Gly
            530                 535                 540

Ala Ser Cys Thr His Tyr Arg Pro Ser Leu Gly Lys Arg Arg Phe Arg
545                 550                 555                 560

Arg Gln Asp Ile Arg His Gly Asn Pro Ala Leu Gln Cys Leu Gly Gln
                565                 570                 575

Ser Gln Glu Glu Glu Ala Val Gly Leu Val Ala Ala Thr Met Val Tyr
            580                 585                 590

Gly Thr Glu His Asn Ser Thr Phe Leu Glu Cys Leu Pro Lys Ser Pro
            595                 600                 605

Gln Ala Ala Val Arg Trp Leu Leu Gln Arg Pro Gly Asp Glu Gly Pro
    610                 615                 620

Asp Gln Val Lys Thr Asp Glu Arg Val Leu His Thr Glu Arg Gly Leu
625                 630                 635                 640

Leu Phe Arg Arg Leu Ser Arg Phe Asp Ala Gly Thr Tyr Thr Cys Thr
                645                 650                 655

Thr Leu Glu His Gly Phe Ser Gln Thr Val Val Arg Leu Ala Leu Val
            660                 665                 670

Val Ile Val Ala Ser Gln Leu Asp Asn Leu Phe Pro Pro Glu Pro Lys
            675                 680                 685

Pro Glu Glu Pro Pro Ala Arg Gly Gly Leu Ala Ser Thr Pro Pro Lys
    690                 695                 700

Ala Trp Tyr Lys Asp Ile Leu Gln Leu Ile Gly Phe Ala Asn Leu Pro
705                 710                 715                 720
```

```
         Arg Val Asp Glu Tyr Cys Glu Arg Val Trp Cys Arg Gly Thr Thr Glu
                         725                 730                 735

Cys Ser Gly Cys Phe Arg Ser Arg Ser Arg Gly Lys Gln Ala Arg Gly
                     740                 745                 750

Lys Ser Trp Ala Gly Leu Glu Leu Gly Lys Lys Met Lys Ser Arg Val
                 755                 760                 765

His Ala Glu His Asn Arg Thr Pro Arg Glu Val Glu Ala Thr
             770                 775                 780

<210> SEQ ID NO 5
<211> LENGTH: 3568
<212> TYPE: DNA
<213> ORGANISM: homo sapiens

<400> SEQUENCE: 5
```

| | | | | | |
|---|---|---|---|---|---|
| acctgggaa | gctctggacc | ctgagtctct | ggaaggactg | gaggcctgag | ggaggcaggg | 60 |
| caagggagg | ttccctcggc | atggagtccc | ctgatgcccc | tgtcccctac | cccaaagcaa | 120 |
| gcctggtgag | ctgagatggg | gcatgtagat | gtggggagag | gctggggtgc | ctggaagcca | 180 |
| gatgggaca | ggcctgggtg | gaagaggctg | ggcagtcatc | tcttgctggc | tctatgaagt | 240 |
| gttgccggac | ctcaaacacc | tgtctaggac | atggcgcccc | ttgggctggg | aatggccctc | 300 |
| cacccttacc | caggggagct | ggagagtctg | gccaaagctt | caggggggctg | gaatatcctg | 360 |
| gaattggggc | agggccagtt | tggaaggtct | ctgctgtggg | cagtggaggg | gcagagaaca | 420 |
| aggcagagcc | cagctaggcc | cctacccagc | ccatcaactt | taacctctga | tccctgacct | 480 |
| cccttccagg | ctctctcccc | acttgtcact | ttgctggagc | ctggggacct | gcatttgtgg | 540 |
| acatctctgt | acacatggcc | tgtgcccctag | ctgggaaggt | cttcccaatg | ggagctggc | 600 |
| cagtgtggca | caaaagcctg | cactgggcca | acaaggtgga | aggagaagcg | gcaggtggac | 660 |
| ggcaaggccc | cagcctcctt | ctctcctccg | cccctcttcc | cgcccaggac | tgggtggagc | 720 |
| cactgcctta | taagtggtgg | cctggtggca | gcagagcaaa | ctacaaccgg | cggccagcgg | 780 |
| gaccagaggg | cggctctgca | ggcaggcggc | agcggtgccc | tcagttcccc | agcatggccc | 840 |
| cctcggcctg | ggccatttgc | tggctgctag | ggggcctcct | gctccatggg | ggtagctctg | 900 |
| gccccagccc | cggccccagt | gtgccccgcc | tgcggctctc | ctaccgagac | ctcctgtctg | 960 |
| ccaaccgctc | tgccatcttt | ctgggccccc | agggctccct | gaacctccag | gccatgtacc | 1020 |
| tagatgagta | ccgagaccgc | ctctttctgg | gtgcctgga | cgccctctac | tctctgcggc | 1080 |
| tggaccaggc | atggccagat | ccccgggagg | tcctgtggcc | accgcagcca | ggacagaggg | 1140 |
| aggagtgtgt | tcgaaaggga | agagatcctt | tgacagagtg | cgccaacttc | gtgcgggtgc | 1200 |
| tacagcctca | caaccggacc | cacctgctag | cctgtgcac | tggggccttc | cagcccacct | 1260 |
| gtgccctcat | cacagttggc | caccgtgggg | agcatgtgct | ccacctggag | cctggcagtg | 1320 |
| tggaaagtgg | ccggggcgg | tgccctcacg | agccagccg | tccctttgcc | agcaccttca | 1380 |
| tagacgggga | gctgtacacg | ggtctcactg | ctgacttcct | ggggcgagag | gccatgatct | 1440 |
| tccgaagtgg | aggtcctcgg | ccagctctgc | gttccgactc | tgaccagagt | ctcttgcacg | 1500 |
| accccggtt | tgtgatggcc | gcccggatcc | ctgagaactc | tgaccaggac | aatgacaagg | 1560 |
| tgtacttctt | cttctcggag | acgtcccct | cgccgatgg | tggctcgaac | catgtcactg | 1620 |
| tcagccgcgt | gggccgcgtc | tgcgtgaatg | atgctggggg | ccagcgggtg | ctggtgaaca | 1680 |
| aatggagcac | tttcctcaag | gccaggctgg | tctgctcggt | gccggccct | ggtggtgccg | 1740 |
| agacccactt | tgaccagcta | gaggatgtgt | tcctgctgtg | gcccaaggcc | gggaagagcc | 1800 |

```
tcgaggtgta cgcgctgttc agcaccgtca gtgccgtgtt ccagggcttc gccgtctgtg    1860
tgtaccacat ggcagacatc tgggaggttt tcaacgggcc ctttgcccac cgagatgggc    1920
ctcagcacca gtgggggccc tatggggca aggtgccctt ccctcgccct ggcgtgtgcc     1980
ccagcaagat gaccgcacag ccaggacggc cttttggcag caccaaggac tacccagatg    2040
aggtgctgca gtttgcccga gcccaccccc tcatgttctg gcctgtgcgg cctcgacatg    2100
gccgccctgt ccttgtcaag acccacctgg cccagcagct acaccagatc gtggtggacc    2160
gcgtggaggc agaggatggg acctacgatg tcattttcct ggggactgac tcagggtctg    2220
tgctcaaagt catcgctctc caggcagggg gctcagctga acctgaggaa gtggttctgg    2280
aggagctcca ggtgtttaag gtgccaacac ctatcaccga atggagatc tctgtcaaaa     2340
ggcaaatgct atacgtgggc tctcggctgg gtgtggccca gctgcggctg caccaatgtg    2400
agacttacgg cactgcctgt gcagagtgct gcctggcccg ggacccatac tgtgcctggg    2460
atggtgcctc ctgtacccac taccgcccca gccttggcaa gcgccggttc cgccggcagg    2520
acatccggca cggcaaccct gccctgcagt gcctgggcca gagccaggaa gaagaggcag    2580
tgggacttgt ggcagccacc atggtctacg cacggagca caatagcacc ttcctggagt     2640
gcctgcccaa gtctccccag gctgctgtgc gctggctctt gcagaggcca ggggatgagg    2700
ggcctgacca ggtgaagacg gacgagcgag tcttgcacac ggagcggggg ctgctgttcc    2760
gcaggcttag ccgtttcgat gcgggcacct acacctgcac cactctggag catggcttct    2820
cccagactgt ggtccgcctg gctctggtgg tgattgtggc ctcacagctg acaacctgt     2880
tccctccgga gccaaagcca gaggagcccc cagcccgggg aggcctggct tccacccac     2940
ccaaggcctg gtacaaggac atcctgcagc tcattggctt cgccaacctg ccccgggtgg    3000
atgagtactg tgagcgcgtg tggtgcaggg gcaccacgga atgctcaggc tgcttccgga    3060
gccggagccg gggcaagcag gccagggca agagctgggc agggctggag ctaggcaaga     3120
agatgaagag ccgggtgcat gccgagcaca atcggacgcc ccgggaggtg gaggccacgt    3180
agaaggggc agaggagggg tggtcaggat gggctggggg gcccactagc agcccccagc     3240
atctcccacc cacccagcta gggcagaggg gtcaggatgt ctgtttgcct cttagagaca    3300
ggtgtctctg ccccccacacc gctactgggg tctaatggag gggctgggtt cttgaagcct    3360
gttccctgcc cttctctgtg ctcttagacc cagctggagc cagcaccctc tggctgctgg    3420
cagccccaag ggatctgcca tttgttctca gagatggcct ggcttccgca acacatttcc    3480
gggtgtgccc agaggcaaga gggttgggtg gttctttccc agcctacaga acaatggcca    3540
ttctgagtga ccctcaaagt gggtgtgt                                       3568
```

<210> SEQ ID NO 6
<211> LENGTH: 276
<212> TYPE: DNA
<213> ORGANISM: homo sapiens

<400> SEQUENCE: 6

```
atgacagact tgtccgagct accatcgaag tcttgggtct gcacgcaaag gatggaatcc     60
cccatctcca ttcccaaaag tttccctacg ggagcctggt gttgtctcct ccggaactgt    120
cctmgcggct gcctgttttt ccctagccat ggttactgcc tgcggggat tcagcctgtg     180
aaggcagtca aggcagttca ccactgtcat caaacctaca cccctgtgtg caygcgcaca    240
cacacttgta acccagtggc acaatgcagg aattag                              276
```

<210> SEQ ID NO 7
<211> LENGTH: 91
<212> TYPE: PRT
<213> ORGANISM: homo sapiens
<220> FEATURE:
<221> NAME/KEY: VARIANT
<222> LOCATION: (1)...(91)
<223> OTHER INFORMATION: Xaa = Any Amino Acid

<400> SEQUENCE: 7

Met Thr Asp Leu Ser Glu Leu Pro Ser Lys Ser Trp Val Cys Thr Gln
1               5                   10                  15

Arg Met Glu Ser Pro Ile Ser Ile Pro Lys Ser Phe Pro Thr Gly Ala
            20                  25                  30

Trp Cys Cys Leu Leu Arg Asn Cys Pro Xaa Gly Cys Leu Phe Phe Pro
        35                  40                  45

Ser His Gly Tyr Cys Leu Arg Gly Ile Gln Pro Val Lys Ala Val Lys
    50                  55                  60

Ala Val His His Cys His Gln Thr Tyr Thr Pro Val Cys Xaa Arg Thr
65                  70                  75                  80

His Thr Cys Asn Pro Val Ala Gln Cys Arg Asn
                85                  90

<210> SEQ ID NO 8
<211> LENGTH: 270
<212> TYPE: DNA
<213> ORGANISM: homo sapiens

<400> SEQUENCE: 8
atgactgaat tgaatgattc taagtgttac gcaattagca aaagatgtct aacaatcact      60
ttggggatcc ggaacaagtg tggtcccagt tcaactgtgt tcctgtcaga atacctctgt    120
ggtgactctc tcctactacg tcagttccag aagcggggga tggaagaccc ctgttgtggc    180
cagcagtgct gttccatgtc ctttccagtg cactgtctcc tctgctgctc agggtcagga    240
tgcccacaca ctcctgcgcc cagcttctga                                     270

<210> SEQ ID NO 9
<211> LENGTH: 89
<212> TYPE: PRT
<213> ORGANISM: homo sapiens

<400> SEQUENCE: 9

Met Thr Glu Leu Asn Asp Ser Lys Cys Tyr Ala Ile Ser Lys Arg Cys
1               5                   10                  15

Leu Thr Ile Thr Leu Gly Ile Arg Asn Lys Cys Gly Pro Ser Ser Thr
            20                  25                  30

Val Phe Leu Ser Glu Tyr Leu Cys Gly Asp Ser Leu Leu Leu Arg Gln
        35                  40                  45

Phe Gln Lys Arg Gly Met Glu Asp Pro Cys Cys Gly Gln Gln Cys Cys
    50                  55                  60

Ser Met Ser Phe Pro Val His Cys Leu Leu Cys Ser Gly Ser Gly
65                  70                  75                  80

Cys Pro His Thr Pro Ala Pro Ser Phe
                85

-continued

<210> SEQ ID NO 10
<211> LENGTH: 2024
<212> TYPE: DNA
<213> ORGANISM: homo sapiens

<400> SEQUENCE: 10

| | | | | | |
|---|---|---|---|---|---|
| agggttagct | cattttttcat | cagggagata | catttctttc | ccaaagctgt | gatctaggag | 60 |
| agttgccaag | cagctagagt | taaaaaaaat | acacaaaaac | cgcaaacaac | ataattcttt | 120 |
| catgtggcat | tctctccttt | gtgctcatca | tgcttgatga | tcgctgacca | gttctaaaat | 180 |
| agagtccatg | ggttcaagcc | tttggctgtt | tctgggctct | tagacactta | gtctcacagc | 240 |
| ttgatcccaa | ataattgtcc | actgacagta | ttcaaagggc | ggaggtgcaa | gactctcttt | 300 |
| ttgtaaggtg | ggactaaatt | ggaaaactat | tgaaattcat | gaaagatttc | tcaggtttac | 360 |
| ttttgtgagc | ttagcacatg | tagaacattt | acaaagcttt | aatgtccata | tctgaacatg | 420 |
| tgtgctcttt | taatcgaaag | tcctcatttt | tttttttttt | tagatccctg | cctatctctt | 480 |
| tgacaggatc | tatagtggtg | gcttaaaacc | taaatgtggt | ctttcttttt | tgctttccag | 540 |
| atctttggca | gggctagtat | gaaacaatcc | aattaacaca | acttgatttc | atctgcttta | 600 |
| ttttgtgatt | atctcttggt | ggccagagcc | agccctctgg | accagaggaa | acaatgatgc | 660 |
| ccacctggtc | aatggaggtt | attttagttg | tgagtactcg | aatttgtctt | gtgtgtaaga | 720 |
| ttccttaaag | aagctgttgt | ttttctgtga | cctaaataag | atactgttcc | caggtaactt | 780 |
| tgggtctaaa | aaatgacctc | tttcttgggg | cctttcagat | gactgaattg | aatgattcta | 840 |
| agtgttacgc | aattagcaaa | agatgtctaa | caatcacttt | ggggatccgg | aacaagtgtg | 900 |
| gtcccagttc | aactgtgttc | ctgtcagaat | acctctgtgg | tgactctctc | ctactacgtc | 960 |
| agttccagaa | gcgggggatg | aagacccct | gttgtggcca | gcagtgctgt | tccatgtcct | 1020 |
| ttccagtgca | ctgtctcctc | tgctgctcag | ggtcaggatg | cccacacact | cctgcgccca | 1080 |
| gcttctgagt | ctcagtctcc | ccttctaggt | cgcctttgca | gcttcactct | ttgtttgctc | 1140 |
| tgtggaagtt | tctcgtttaa | gctctgttga | gtgaaaagag | tgatcacaac | cccattggca | 1200 |
| ttttgttttc | tgtttctgcg | ttaattcacc | taggacaatg | gcctccagct | gcatccatac | 1260 |
| tgctgcaaat | gacatgattt | cactcttttt | tatggctgtg | tagttccatg | gtatatacat | 1320 |
| atatcacatt | ttctttaccc | agttcaccat | tgatgggcac | ctgggtttat | cccatgtcct | 1380 |
| tgctattgtg | aatagtgctg | tgatgaacat | gtacatgcat | atgtcttttt | ggtaaaatga | 1440 |
| tttattttcc | ttcgggggta | tatgcagtaa | tgggattgct | gggtcaagtg | gtagttttat | 1500 |
| ttttagttct | ttagaaattt | ccaaatgctt | tccataggga | ctgagctaat | ttacttttcc | 1560 |
| accaacagtg | tataagtgtt | cccttttgtat | gcattctcac | caacatctat | tttttgactt | 1620 |
| tttagtaata | gccattctga | ctggtgtgag | atgatatctc | atttggtttt | ggtttacatt | 1680 |
| ttcctgacaa | ttagtgatac | taagcatttt | tcatgtttgt | tggctgcttg | tatgtcttct | 1740 |
| ttttaagaag | tgactgttca | tgtcatttgc | ccacttttta | atttggttgt | tttttgcttg | 1800 |
| ttgaattatt | taagttactt | atagattctg | agtgtttgcc | ctttgtagga | cgtatagttt | 1860 |
| gcaaatattt | tctcccattc | tgcaggttgt | ctgtttagtt | taatagtttc | ttttttttgct | 1920 |
| gtgcagaaag | tctttagttt | aattaggtcc | catttatcaa | ttttttgtttt | tgttgcaatt | 1980 |
| gcttttgagg | gttcagtttt | attattctgt | atatggatgg | tcag | | 2024 |